United States Patent
Satyaraj et al.

(10) Patent No.: US 11,102,952 B2
(45) Date of Patent: Aug. 31, 2021

(54) METHODS FOR ENABLING PET OWNERSHIP

(71) Applicant: NESTEC SA, Vevey (CH)

(72) Inventors: Ebenezer Satyaraj, Wildwood, MO (US); Peichuan Sun, St. Louis, MO (US); Scott Sherrill, Chesterfield, MO (US); Qinghong Li, Chesterfield, MO (US); Steven Hannah, Chesterfield, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 421 days.

(21) Appl. No.: 15/984,857

(22) Filed: May 21, 2018

(65) Prior Publication Data

US 2018/0338467 A1    Nov. 29, 2018

Related U.S. Application Data (60) Provisional application No. 62/510,842, filed on May 25, 2017.

(51) Int. Cl.
| | |
|---|---|
| *G01N 33/68* | (2006.01) |
| *A61B 5/00* | (2006.01) |
| *A01K 1/00* | (2006.01) |
| *A01K 1/03* | (2006.01) |
| *A01K 1/01* | (2006.01) |

(52) U.S. Cl.
CPC .............. *A01K 1/0052* (2013.01); *A01K 1/03* (2013.01); *G01N 33/6893* (2013.01); *A01K 1/0107* (2013.01); *A61B 5/411* (2013.01); *G01N 2800/24* (2013.01)

(58) Field of Classification Search
None
See application file for complete search history.

(56) References Cited

U.S. PATENT DOCUMENTS

| | | |
|---|---|---|
| 2013/0236475 A1 | 9/2013 | Wells et al. |
| 2015/0175940 A1 | 6/2015 | Wells et al. |
| 2016/0146808 A1 | 5/2016 | Nelson et al. |

OTHER PUBLICATIONS

Kelly et l. 'Fel d 1 and Fel d 4 levels in cat fur, saliva, and urine.' J Allergy Clin Immunol vol. 142, No. 6, 2018.*
Kelly et al. 'Stabilizing Fel d1 Levels in a Cat Allergen Exposure Chamber.' Journal of Allergy and Clinical Immunology, suppl. S; St. Louis vol. 141, Iss. 2, (Feb. 1, 2018): AB126. DOI:10.1016/j.jaci. 2017.12.401.*
Santorina Do hypoallergenic cats exist?—Secretion of Fel d 1 in the Neva Masquarade versus domestic cat breeds. 2013 http://othes. univie.ac.at/30992/1/2014-01-08_0801928.pdf Available online Jan. 8, 2014.*
Berkowitz et al. 'Efficacy of fexofenadine in the prophylactic control of cat allergen-induced allergic rhinitis.' Annals of Allergy, Asthma & Immunology vol. 96, Issue 2, Feb. 2006, pp. 327-333.*
Wentz et al. 'Variability of cat allergen shedding.' J. Allerg. Clin. Immunol. 85(1):94-98, 1990.*
Butt, et al. "Do hypoallergenic cats and dogs exist?" Annals of Allergy, Asthma & Immunology vol. 108, No. 2 Dec. 6, 2011.
International Search Report and Written Opinion PCT/IB2018/ 053573, dated Aug. 10, 2018.

\* cited by examiner

*Primary Examiner* — Nora M Rooney (57) ABSTRACT

The present disclosure provides methods for enabling an individual having a cat allergy to have a cat as a pet. Such a method can include quantitatively determining a threshold in the individual for an environmental level of an allergen produced by the cat and selecting a cat or a breed of cat that creates an environmental level of the allergen that is less than the threshold. Additionally, such a method can include lowering the allergens disseminated by the cat by treating the environment inhabited by the cat during a time period where the cat expresses elevated allergens.

6 Claims, 6 Drawing Sheets

METHODS FOR ENABLING PET OWNERSHIP

CROSS REFERENCE TO RELATED APPLICATIONS

This application claims priority to U.S. Provisional Application No. 62/510,842 filed May 25, 2017, the disclosure of which is incorporated herein by this reference.

BACKGROUND

Cat allergens are produced by cats and can affect pet owners. Allergens can be spread throughout the environment inhabited or frequented by the cat including litter boxes, bedding, counters, floors, etc.

Symptoms of cat allergies range from mild rhinitis and conjunctivitis to life-threatening asthmatic responses, and cat allergies are a major roadblock to cat ownership. For example, cat allergy is the primary reason given by cat owners for returning cats to animal shelters.

Most cat allergies are caused by a small stable glycoprotein called Fel d1 (*Feline domesticus* allergen number 1). Cat allergens such as Fel d1 can be released from the litter box into the surrounding area. For example, cats often scratch and shift the cat litter, creating dust by which the cat allergens become airborne in the surrounding area. Similarly, scooping the cat litter can circulate cat allergens into the air.

Fel d1 can be particularly problematic because it is lightweight (35 kDa) and thus remains suspended in the air for an extended amount of time. Furthermore, Fel d1 is a sticky protein and consequently adheres to articles within the area surrounding the litter box, such as carpets, walls, furniture, clothing, and curtains, thereby making this allergen difficult to remove after it has circulated from the litter box.

SUMMARY

The present disclosure relates generally to enabling an individual having a cat allergy to have a cat as a pet. Additionally, such methods can be used for matching prospective pet owners to prospective pets.

Accordingly, in a general embodiment, a method of enabling an individual having a cat allergy to have a cat as a pet can comprise quantitatively determining a threshold in the individual for an environmental level of an allergen produced by the cat and selecting a cat or a breed of cat that produces an environmental level of the allergen that is less than the threshold.

Additionally, in another embodiment, a method of enabling an individual having a cat allergy to have a cat as a pet can comprise lowering the allergens disseminated by the cat by treating the environment inhabited by the cat during a time period where the cat expresses elevated allergens.

Further, in still another embodiment, a method of enabling an individual having a cat allergy to have a cat as a pet can comprise identifying a cat from a plurality of cats based on the identified cat producing less allergen relative to the other cats of the plurality of cats.

Yet, in another embodiment, a method of matching a prospective cat owner to a cat can comprise of identifying a cat from a plurality of cats based on the identified cat producing less allergen relative to the other cats of the plurality of cats.

Additional features and advantages are described herein and will be apparent from the following Detailed Description and the Figures.

DETAILED DESCRIPTION

As used in this disclosure and the appended claims, the singular forms "a," "an" and "the" include plural referents unless the context clearly dictates otherwise. The words "comprise," "comprises" and "comprising" are to be interpreted inclusively rather than exclusively. Likewise, the terms "include," "including" and "or" should all be construed to be inclusive, unless such a construction is clearly prohibited from the context. However, the devices disclosed herein may lack any element that is not specifically disclosed. Thus, a disclosure of an embodiment using the term "comprising" includes a disclosure of embodiments "consisting essentially of" and "consisting of" the components identified.

The term "pet" means any animal which can produce and/or carry an allergen. The pet can be an avian, bovine, canine, equine, feline, hicrine, lupine, murine, ovine, or porcine animal. The pet can be any suitable animal, and the present disclosure is not limited to a specific pet animal. The term "companion animal" means a dog or a cat.

While the terms "individual," "subject" and "patient" are often used herein to refer to a human, the present disclosure is not so limited. Accordingly, these terms refer to any animal, mammal or human.

Ranges are used herein in shorthand to avoid listing every value within the range. Any appropriate value within the range can be selected as the upper value or lower value of the range. Moreover, the numerical ranges herein include all integers, whole or fractions, within the range.

All percentages expressed herein are by weight of the total weight of the food composition unless expressed otherwise. When reference is made to the pH, values correspond to pH measured at 25° C. with standard equipment. As used herein, "about" or "substantially" in reference to a number is understood to refer to numbers in a range of numerals, for example the range of −10% to +10%, preferably −5% to +5%, more preferably −1% to +1%, and even more preferably −0.1% to +0.1% of the referenced number.

The methods and devices and other advances disclosed herein are not limited to particular methodologies, protocols, and reagents because, as the skilled artisan will appreciate, they may vary. Further, the terminology used herein is for the purpose of describing particular embodiments only and does not limit the scope of that which is disclosed or claimed.

Unless defined otherwise, all technical and scientific terms, terms of art, and acronyms used herein have the meanings commonly understood by one of ordinary skill in the art in the field(s) of the present disclosure or in the field(s) where the term is used. Although any compositions, methods, articles of manufacture, or other means or materials similar or equivalent to those described herein can be used, the preferred devices, methods, articles of manufacture, or other means or materials are described herein.

In one embodiment, a method of enabling an individual having a cat allergy to have a cat as a pet can comprise quantitatively determining a threshold in the individual for an environmental level of an allergen produced by the cat; and selecting a cat or a breed of cat that creates an environmental level of the allergen that is less than the threshold.

Generally, the allergen can be any allergen produced by the cat. In one embodiment, the allergen is Fel d1. Additionally, in one embodiment, quantitatively determining a threshold can include positioning a first allergen source comprising the allergen in a chamber, distributing the allergen from the allergen source in the chamber, having the individual in the chamber, and measuring the symptoms of the individual, as described herein. In one aspect, the allergen source can comprise a predetermined concentration of the allergen and the individual is symptomatic at the predetermined concentration, thereby providing the threshold of the individual. Additionally, in another aspect, the distributing of the allergen can be performed for a predetermined time period. In one embodiment, quantitatively determining a threshold can include exposing the individual to a predetermined concentration of allergen from an allergen source such that the individual is symptomatic, thereby providing the threshold of the individual.

The allergen source can be any material having the cat allergen. In one embodiment, the allergen source can be cat hair and the exposing of the allergen can be performed for a predetermined time period.

Generally, the present methods can be used with any cat or to match any cat with any prospective owner. As such, in generally, cats can be quantified as high, medium, and low allergen producers where high allergen producers produce an average salivary Fel d1 concentration from 10 to 100, or higher, µg/ml, where medium allergen producers produce a salivary Fel d1 concentration between 5 and 10 µg/ml, and where low allergen producers produce a salivary Fel d1 concentration between 0.01 and 5 µg/ml. In some aspects, the cat can produce a salivary Fel d1 concentration of less than 4, 3, 2, or even 1 µg/ml. In other aspects, the cat can produce a salivary Fel d1 concentration of more than 10, 15, 20, 25, 30, or even 50 µg/ml. While the threshold can be individually determined for any subject, in one embodiment, the threshold can be higher than the Fel d1 concentration present in an environment, such as a home, where the cat is a high allergen producer. In one aspect, the cat can be a medium allergen producer. In another aspect, the cat can be a low allergen producer.

In another embodiment, a method of enabling an individual having a cat allergy to have a cat as a pet can comprise lowering the allergens disseminated by the cat by treating the environment inhabited by the cat during a time period where the cat expresses elevated allergens.

Lowering the allergens or treating the environment can be by any method that removes or degrades the allergen, or otherwise inhibits the binding of the allergen in a human. In one embodiment, treating the environment can include shampooing the cat to remove allergen from the cat. In another embodiment, treating the environment can include wiping, contacting, or cleaning a member selected from the group consisting of counters, floors, furniture, bedding, and walls, with an antibody that binds to the allergen. In still another embodiment, treating the environment includes oral administering to the cat antibodies that bind to the allergens. In one aspect, the antibodies can be polyclonal antibodies. In another aspect, the antibodies can be part of a food composition. Generally, the elevated allergens can be measured as a correlation to an average salivary Fel d1 concentration produced by the cat. In one aspect, the allergens can be lowered by at least 50%. In other aspects, the allergens can be lowered by 60%, 70%, 80%, 90%, 95%, or even 99%.

While the present methods can be used at any time during the year, the present inventors have discovered that some cats can produce a season high allergen load at specific periods of year. As such, in one embodiment, the time period can be from November to February. In another aspect, the time period can be from July to September. Regardless of time period, the present methods include enabling cat ownership by treating a cat having elevated levels of Fel d1 whether it be at a specific time of the year or a period specific to an individual cat.

In addition to the above, a method of enabling an individual having a cat allergy to have a cat as a pet or a method of matching a prospective cat owner to a cat can comprise identifying a cat from a plurality of cats based on the identified cat producing less allergen relative to the other cats of the plurality of cats. In one aspect, the cat can be a high Fel d1 producer. In another aspect, the cat can be a medium Fel d1 producer. In still another aspect, the cat can be a low Fel d1 producer.

Various apparatuses can be used to determine the threshold of an owner or prospective owner as well as environment level produced by the cat. The following description provides an example of such apparatuses.

Figure 1:
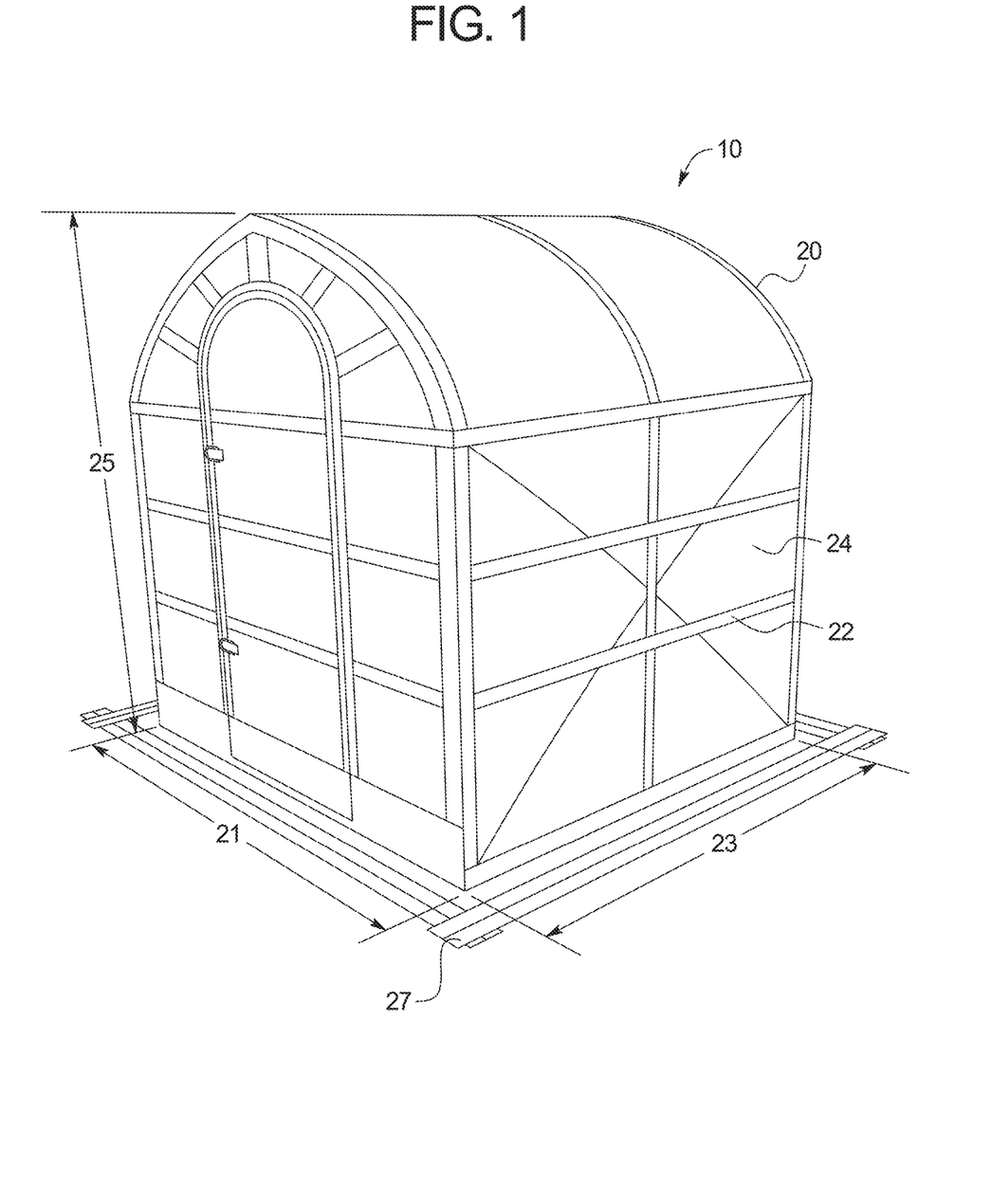
FIG. 1 shows a perspective view of an embodiment of an apparatus provided by the present disclosure.
Figure 2:
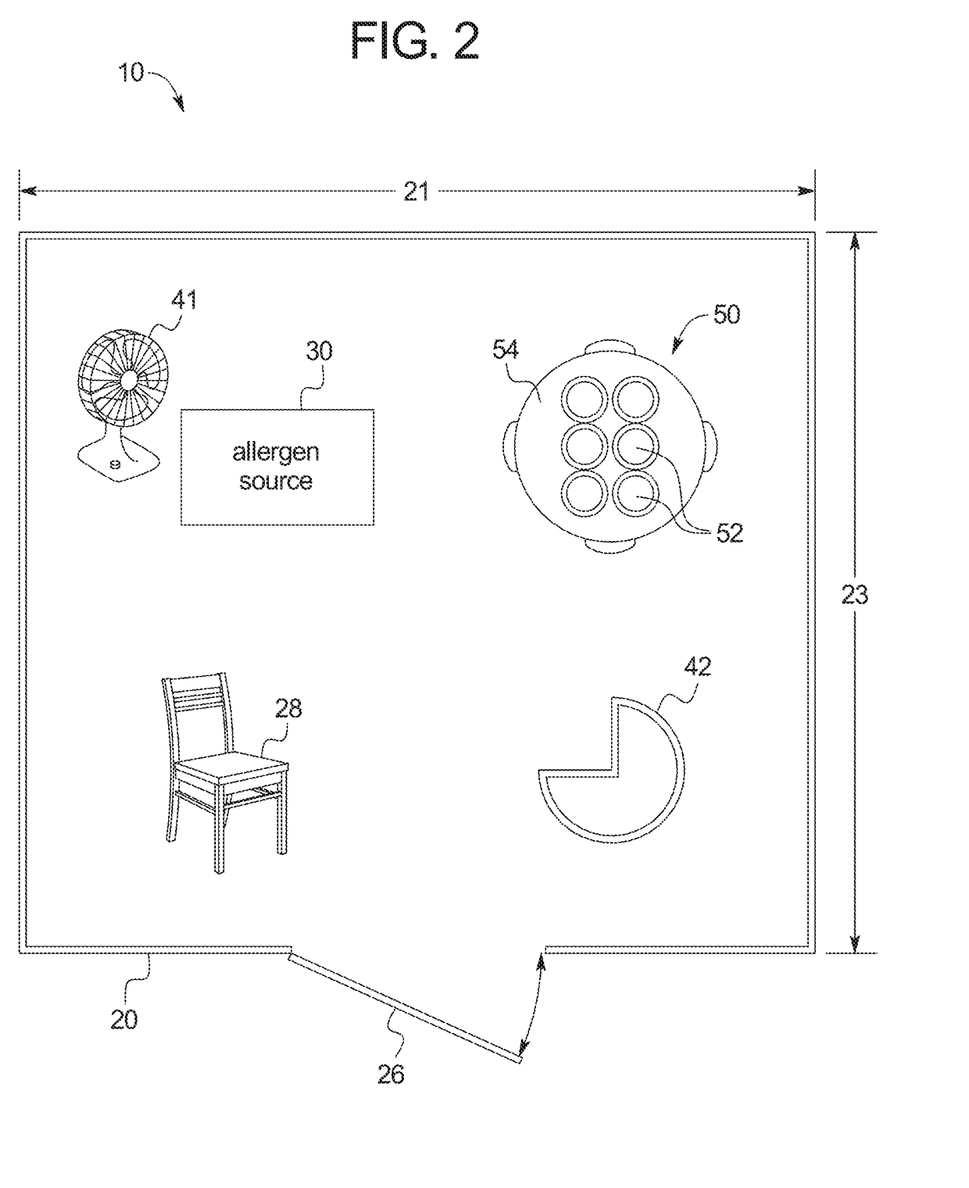
FIG. 2 shows a schematic diagram of an embodiment of an apparatus provided by the present disclosure.

FIGS. 1 and 2 generally illustrate an embodiment of an apparatus 10 provided by the present disclosure. The apparatus 10 can generate and can measure environmental levels of an allergen as discussed in detail hereafter. The apparatus 10 can comprise a housing 20, an allergen source 30, and an air circulation device 41. The housing 20 is preferably portable; in an embodiment, the housing 20 is a collapsible tent. As used herein, a "collapsible" article is capable of being configured into a smaller size without causing damage to the article, preferably without the need for tools.

The housing 20 can form a chamber. Although the housing 20 can be air-tight, the housing 20 does not have to be air-tight, and an embodiment of the housing 20 merely forms a closed system such that the tested allergen does not exit the interior of the housing 20 during use of the apparatus 10 and additional allergen does not enter the interior of the housing 20 during use of the apparatus 10.

As shown in FIG. 1, the housing 20 can comprise a frame 22 that supports a shell 24 to form the chamber. In an embodiment, the frame 22 is made of a metal material. Preferably the shell 24 is made of non-porous material. The shell 24 can define the interior of the housing 20. For example, the shell 24 can form a majority of the outer surface of the housing 20 (e.g. substantially all of the outer surface of the housing 20) and/or a majority of the inner surface of the housing 20 (e.g. substantially all of the inner surface of the housing 20).

Preferably at least a portion of the housing 20 can be folded to enable transportation and compact storage. For example, at least a portion of the frame 22 and/or at least a portion of the shell 24 can be folded to enable transportation and compact storage of the housing 20. The housing 20 can be arranged in (i) an operative configuration in which the housing 20 defines an interior and (ii) a storage/transport configuration in which the housing 20 defines an interior that is smaller relative to the operative configuration or in which the housing 20 does not define an interior e.g. the housing 20 is folded completely upon itself. For example, the frame 22 can comprise one or more poles that can be configured in (i) an operative configuration in which the poles are inserted into each other at their ends to form a substantially rigid and/or stable arrangement and (ii) a storage/transport configuration in which the poles are in a compact arrangement, such as laying side-by-side with each other. The poles can be hollow and connected to each other by one or more cords, such as rubber ropes, that pass through the interiors of the poles to enable a user to move the housing 20 between configurations and arrange the housing 20 in the desired configuration.

The shell 24 is preferably flexible; for example, the shell 24 can comprise a fabric such as polyester, a plastic such as flexible polyvinyl, and/or linoleum. The shell 24 can be made of a material that can be easily cleaned, for example with isopropyl or ethanol solutions, such that no measurable allergen remains in the housing 20 after cleaning. In an embodiment, the housing 20 is at least partially disposable; for example, the frame 22 and/or the shell 24 can be disposable. As used herein, a "disposable" article is designed for a single use after which it is recycled or is disposed as solid waste. For example, a disposable article is not permanently fixed in position in a building, and a disposable article can be moved from its position without damaging the article.

The shell 24 can be connected to the frame 22 to form the housing 20. For example, a portion of the shell 24 can be reversibly attachable to and removable from the frame 22. Alternatively or additionally, a portion of the shell 24 can be fixedly attached to and/or integral with the frame 22. The shell 24 can comprise a door 26 that opens and closes, for example by a zipper. The bottom of the shell 24 can be secured to a solid surface, for example by floor tape 27. In an embodiment, the shell 24 does not have an integrated floor; additionally or alternatively, a portion of the shell 24 can comprise an integrated floor. If the bottom of the shell 24 is secured to a solid surface, preferably the solid surface does not have carpet.

Referring again to FIGS. 1 and 2, the housing 20 in the operative configuration can have any size, preferably at least large enough to contain a human seated on a chair or stool 28. The housing 20 in the operative configuration can have a width 21. As non-limiting examples, the width 21 can be at least three feet, preferably at least four feet, more preferably at least five feet, most preferably at least six feet, and/or the width 21 can be at most nine feet, preferably at most eight feet, more preferably at most seven feet. In an embodiment, the width 21 is about six feet, but the housing 20 in the operative configuration is not limited to a specific distance of the width 21.

The housing 20 in the operative configuration can have a depth 23 perpendicular to the width 21. As non-limiting examples, the depth 23 can be at least three feet, preferably at least four feet, more preferably at least five feet, most preferably at least six feet, and/or the depth 23 can be at most nine feet, preferably at most eight feet, more preferably at most seven feet. In an embodiment, the depth 23 is about six feet, but the housing 20 in the operative configuration is not limited to a specific distance of the depth 23.

As shown in FIG. 1, the housing 20 in the operative configuration can have a height 25. As non-limiting examples, the height 25 can be at least four feet, preferably at least five feet, more preferably at least six feet, and/or the height 25 can be at most ten feet, preferably at most nine feet, more preferably at most eight feet. In an embodiment, the height 25 is about seven feet, but the housing 20 in the operative configuration is not limited to a specific distance of the height 25. Preferably the width 21 is substantially the same for the majority of the height 25 of the housing 20 and/or the depth 23 is substantially the same for the majority of the height 25 of the housing 20, although the housing 20 can taper at the top end thereof in a non-limiting embodiment shown in FIG. 1.

As noted above, the housing 20 in the transport/storage configuration defines an interior that is smaller relative to the operative configuration or does not define an interior e.g. the housing 20 is folded completely upon itself. For example, at least one of the width 21, the depth 23 or the height 25 is less in the transport/storage configuration than the operative configuration, and preferably all three are less in the transport/storage configuration than the operative configuration. In an embodiment, the housing 20 in the transport/storage configuration can be positioned within and carried by a conventional backpack.

Referring to FIG. 2, the allergen source 30 can be positioned within the housing 20. The allergen source 30 can be any source of an allergen, preferably an allergen from a pet, more preferably from a companion animal, most preferably from a cat. For example, the allergen source 30 can be a cat litter box that contains cat litter soiled by urine and/or feces. As another example, the allergen source 30 can be an open container in which cat hair is positioned. An "allergen" is any substance that can produce an immune response in some individuals but is otherwise harmless to such individuals.

The air circulation device 41 can be positioned within the housing 20. The air circulation device 41 can be any device that suspends and/or distributes at least a portion of the allergen from the allergen source 30. For example, the air circulation device 41 can be at least one mechanical fan comprising a rotating arrangement of vanes or blades that extend from a hub. In a preferred embodiment, the air circulation device 41 can comprise a primary fan, and the apparatus 10 can comprise an additional air circulation device 42 that can comprise a secondary fan such as an oscillating fan. An "oscillating fan" is a fan for which the hub rotates on at least two axes, namely the axis of rotation of the vanes/blades and another axis that is different than the axis of rotation of the vanes/blades. Preferably the other axis of the oscillating fan is perpendicular to the axis of rotation of the vanes/blades.

The air circulation device 41 and the additional air circulation device 42 can direct air to circulate the allergen from the allergen source 30 into the environment of the interior of the housing 20. For example, the air circulation device 41 can be positioned to blow or otherwise direct air at and/or across the allergen source 30, and the additional air circulation device 42 can be positioned on the directly opposite side of the allergen source 30 from the air circulation device 41 to blow or otherwise direct air in the opposite direction and thus produce air turbulence adjacent to and/or above the allergen source 30. This air turbulence can maintain particles from the allergen source 30 in suspension in the environment of the interior of the housing 20 during testing. For example, in an embodiment where the allergen source 30 comprises a cat litter box, the air turbulence from the air circulation device 41 and the additional air circulation device 42 can distribute and/or suspend cat litter particles in the interior of the housing 20.

The apparatus 10 can comprise a collection device 50 that can be positioned within the housing 20. The collection device 50 can be any device capable of collecting the allergen and/or particles comprising the allergen. In an embodiment, the collection device 50 comprises one or more petri plates 52. As a non-limiting example, the one or more petri plates 52 can comprise 10 cm petri plates pre-coated with a 2% gelatin solution from cold water fish skin. The one or more petri plates 52 can be positioned adjacent to each other or in different locations in the housing 20. As a non-limiting example, some of the petri plates 52 can be positioned on the floor approximately 10 cm from the edge of the allergen source 30, and some of the petri plates 52 can be positioned on a table 54, such as a 1 m table approximately 1 m from the allergen source 30.

The air circulation device 41 and the additional air circulation device 42 can be activated for a predetermined time period, and the material collected by the collection apparatus 50 can be extracted after the predetermined time period. The collected material can be extracted using any compound capable of removing the allergen from the collection device 50, for example a solution of phosphate buffered saline, 0.1% polysorbate 20 such as TWEEN® 20, and 0.15% antimicrobial such as KATHON® ("PBS-Tk").

Then the material extracted from the collection device 50 can be assayed to determine the quantity of allergen emitted from the allergen source 30 during the predetermined time period. In an embodiment, the extracted material can be assayed to determine the quantity of Fel d1 emitted from a soiled cat litter box during a predetermined time period. For example, the extracted material can be assayed for Fel d1 using a commercially available Fel d1 enzyme-linked immunosorbent assay (ELISA) kit such as Product Code EL-FD1 from Indoor Biotechnologies. The allergen can be quantitated as ng/plate/hour.

As discussed in further detail in Example 1 later in this application, the present inventors verified the effectiveness of the apparatus 10. For example, two soiled litter boxes from the same cat were used for different amounts of time (in days). The longer the cat had used the litter box (allergen source 30), the higher the level of Fel d1 that was emitted into the housing 20 by the litter box (allergen source 30), collected by the collection device 50, and quantitated by assay.

In a preferred embodiment, the apparatus 10 is configurable. For example, one or more of the allergen source 30, the air circulation device 41, the additional air circulation device 42, or the collection device 50 can be movable relative to the housing 20 e.g. not fixedly attached to the housing 20. As another example, the shell 24 can comprise portals for sampling or injecting allergen e.g. at least a portion of the allergen source 30 can be positioned exterior relative to the housing 20, and/or at least a portion of the collection device 50 can be positioned exterior relative to the housing 20. As yet another example, a pipe can be attached to and/or insert through the shell 24. The pipe can be used to establish and/or maintain a desired pressure in the interior of the housing 20, for example a positive pressure, a negative pressure, or an ambient pressure. If a pipe is used, preferably the apparatus 10 still provides the closed system in which the tested allergen does not exit the interior of the housing 20 during use of the apparatus 10 and additional allergen does not enter the interior of the housing 20 during use of the apparatus 10.

Figure 3:
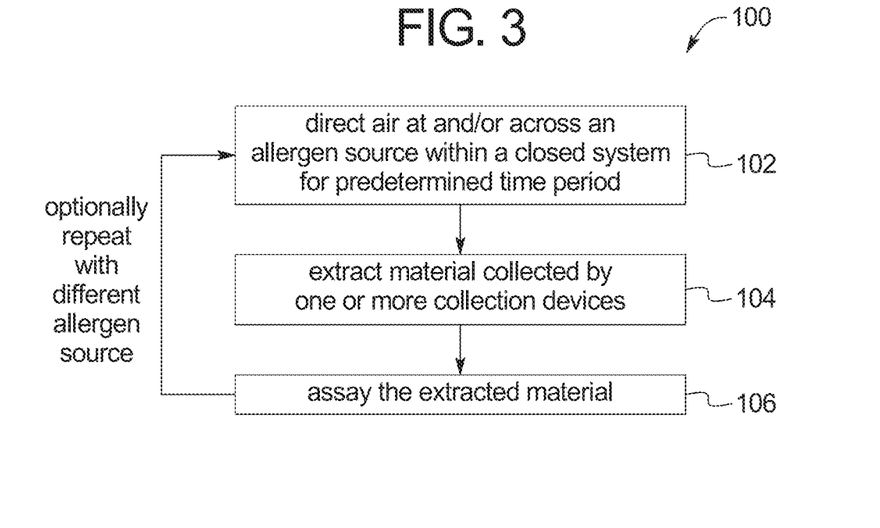
FIG. 3 shows a flowchart of an embodiment of a method provided by the present disclosure.

Another aspect of the present disclosure is a method 100 of generating and measuring environmental levels of an allergen, for example an allergen from a companion animal such as a cat. An embodiment of the method 100 is generally illustrated in FIG. 3. The method 100 can employ the apparatus 10 and/or another apparatus.

In Step 102, air can be directed at and/or across a first allergen source that is preferably contained within a chamber that provides a closed system. The chamber can contain one or more collection devices. Additionally or alternatively, one or more collection devices can be outside of the chamber but have access to the interior of the chamber through one or more portals. Step 102 is preferably performed for a predetermined time period.

One or more air circulation devices, preferably positioned within the chamber, can direct the air at and/or across the first allergen source during Step 102. The one or more air circulation devices can be any device capable or suspending and/or distributing the allergen in the chamber. In an embodiment, a primary fan can be positioned to blow or otherwise direct air at and/or across the first allergen source. A secondary oscillating fan can be positioned on the directly opposite side of the first allergen source from the primary fan to blow or otherwise direct air in the opposite direction and thus produce air turbulence adjacent to and/or above the first allergen source. This air turbulence can maintain particles from the first allergen source in suspension in the environment of the interior of the housing during testing.

In Step 104, material collected by the one or more collection devices can be extracted, for example after Step 102 is completed. Each of the one or more collection devices can be any device capable of collecting the allergen and/or particles comprising the allergen. For example, the one or more collection devices can comprise petri plates at various positions within the chamber. The material can be extracted using any compound capable of removing the allergen from the one or more collection devices, for example a phosphate-buffered solution.

In Step 106, the extracted material can be assayed to determine the quantity of the allergen collected by the one or more collection devices. Any assay capable of identifying a quantity of the allergen can be used, for example an ELISA kit. The quantity of the allergen collected by the one or more collection devices during the test can be indicative of the quantity of allergen emitted by the allergen source during the test.

In an embodiment, the method 100 can measure the effectiveness of various approaches implemented to reduce environmental levels of an airborne allergen. In such an embodiment, the method 100 can be repeated with a second allergen source that is different than the first allergen source. In such an embodiment, Steps 102, 104 and 106 are preferably performed the same as they were previously performed, other than the different allergen sources.

The second allergen source can be a cat litter box that has been subjected to at least one different condition than the first cat litter box and/or has at least one different characteristic relative to the first cat litter box. For example, the first allergen source can be a first cat litter box used by a first specific cat, and the second allergen source can be a second cat litter box used by a second specific cat. Other than the different specific cats, the first and second cat litter boxes can be subjected to one or more same or similar conditions, for example the same type of cat litter, one or more of the same location, the same time period of use, or the same amount of waste matter deposited therein. In this example, the method 100 can determine which of the specific cats sheds less allergen. By using the method 100 to measure which specific cat sheds less allergen, an individual can select a cat that minimizes or prevents the individual's exposure to the allergen.

As another example, the first allergen source can be a first cat litter box used by a first breed of cat, and the second allergen source can be a second cat litter box used by a second breed of cat. Other than the different breeds of cat, the first and second cat litter boxes can be subjected to one or more same or similar conditions, for example the same type of cat litter, one or more of the same location, the same time period of use, or the same amount of waste matter deposited therein. In this example, the method 100 can determine which breed of cat sheds less allergen. By using the method 100 to measure which breed of cat sheds less allergen, an individual can select a breed of cat that minimizes or prevents the individual's exposure to the allergen.

As yet another example, the first allergen source can be a first cat litter box containing a first type of cat litter, and the second allergen source can be a second cat litter box containing a second type of cat litter. Other than the different types of cat litter, the first and second cat litter boxes can be subjected to one or more same or similar conditions, for example one or more of the same location, the same time period of use, the same amount of waste matter deposited therein, use by the same breed of cat, or use by the same specific cat. In this example, the method 100 can determine which of the first and second types of cat litter is more effective at preventing emission of the allergen from the litter box. By using the method 100 to measure which type of cat litter is more effective at preventing emission of the allergen from the litter box, an individual can select a type of cat litter that minimizes or prevents the individual's exposure to the allergen.

As still another example, the first allergen source can be a first cat litter box used by a cat that has been provided a first diet, and the second allergen source can be a second cat litter box used by a cat that has been provided a second diet. The cat that has been provided the first diet can be the same breed or the same specific cat as the cat that has been provided the second diet. Other than the different diets of the cat(s), the first and second cat litter boxes can be subjected to one or more same or similar conditions, for example one or more of the same location, the same time period of use, the same amount of waste matter deposited therein, the same type of cat litter, use by the same breed of cat, or use by the same specific cat. In this example, the method 100 can determine which of the first and second diets results in the cat producing less of the allergen relative to the other diet. By using the method 100 to measure which diet is more effective at preventing allergen production, an individual can administer a diet to the cat that minimizes or prevents the individual's exposure to the allergen.

As an even further example, the first allergen source can be an allergen source that collected allergen in a first location, such as a first room of a house, and the second allergen source can be an allergen source that collected allergen in a second location different than the first location, such as a second room of the house. Other than the location at which the allergen sources are positioned, the first and second allergen sources can be subjected to one or more same or similar conditions, for example the same time period of use and/or use by the same specific cat. In this example, the method 100 can determine which of the locations contains less of the allergen relative to the other location. By using the method 100 to determine which location contains more allergen, an individual can avoid the location to thereby minimize or prevent exposure to the allergen.

The second allergen source can be used in the same chamber as the first allergen source after the testing of the first allergen source is completed and preferably after the chamber is cleaned. Alternatively, the second allergen source can be used in a different chamber than the first allergen source, for example substantially contemporaneously; the chambers are preferably substantially the same, for example the same dimensions and/or the same materials.

Figure 4:
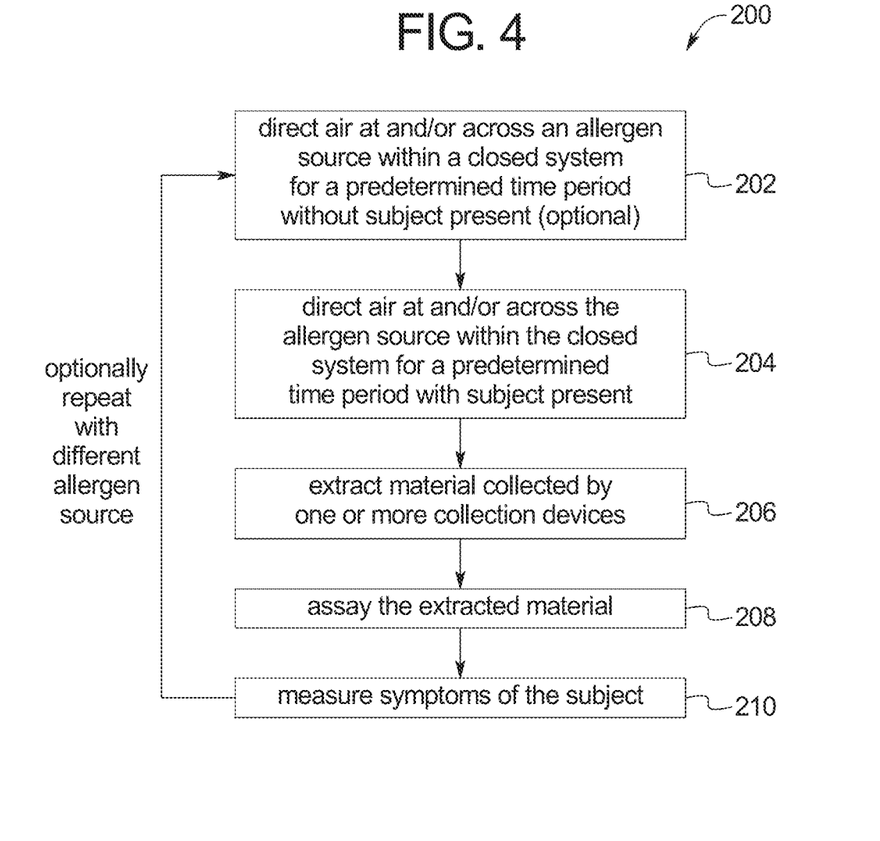
FIG. 4 shows a flowchart of an embodiment of a method provided by the present disclosure.

In another embodiment, a method 200 can expose a subject, preferably one or more human subjects, to an allergen to evaluate the symptoms of the subject. The method 200 can employ the apparatus 10 and/or another apparatus.

In Step 202, which is optional, the subject is absent while a chamber that provides a closed system is loaded with an allergen. In an embodiment, the subject can be absent during a predetermined time in which air is directed at and/or across a first allergen source contained within the chamber. For example, the allergen can be distributed in the apparatus for a predetermined time period without the subject, such as thirty-six hours.

The chamber can contain one or more collection devices. Additionally or alternatively, one or more collection devices can be outside of the chamber but have access to the interior of the chamber through one or more portals.

In Step 204, the subject is present in the chamber that provides a closed system while the allergen is distributed and/or circulated therein. In an embodiment, the subject can be present in the chamber during a predetermined time in which air is directed at and/or across a first allergen source contained within the chamber. For example, the subject can be within the chamber with the allergen circulating for a predetermined time period, such as four to eight hours.

One or more air circulation devices, preferably positioned within the chamber, can direct the air at and/or across the first allergen source during Steps 202 and 204. The one or more air circulation devices can be any device capable or suspending and/or distributing the allergen in the chamber. In an embodiment, a primary fan can be positioned to blow or otherwise direct air at and/or across the first allergen source. A secondary oscillating fan can be positioned on the directly opposite side of the first allergen source from the primary fan to blow or otherwise direct air in the opposite direction and thus produce air turbulence adjacent to and/or above the first allergen source. This air turbulence can maintain particles from the first allergen source in suspension in the environment of the interior of the housing during testing.

In Step 206, material collected by the one or more collection devices can be extracted, for example after Step 204 is completed. Each of the one or more collection devices can be any device capable of collecting the allergen and/or particles comprising the allergen. For example, the one or more collection devices can comprise petri plates at various positions within the chamber. The material can be extracted using any compound capable of removing the allergen from the one or more collection devices, for example a phosphate-buffered solution.

In Step 208, the extracted material can be assayed to determine the quantity of the allergen collected by the one or more collection devices during the test. Any assay capable of identifying a quantity of the allergen can be used, for example an ELISA kit. The quantity of the allergen collected by the one or more collection devices during the test can be indicative of the quantity of allergen emitted by the allergen source during the test.

In Step 210, the symptoms, if any, of the subject in response to the airborne allergen can then be evaluated to determine the sensitivity of the subject to the allergen. The symptoms, if any, of the subject can be correlated to the quantity of the allergen emitted from the allergen source during these test.

The method 200 can measure the symptoms of the subject at various environmental levels of the allergen. In such an embodiment, Steps 202, 204, 206 and 208 can be repeated, for example with the predetermined time period of Step 204 being different, or with a second allergen source different from the first allergen source (subjected to at least one different condition and/or has at least one different characteristic, e.g. the amount of the allergen in the allergen source is different). The method 200 can be used determine a threshold amount of allergen at which symptoms are induced in the subject. The threshold amount of allergen for the subject can be used to select an appropriate pet for the subject to own, for example a specific breed of cat or a specific cat, such that the pet does not induce allergic symptoms in the subject or induces tolerable allergic symptoms in the subject.

In an embodiment of the method 200, a predetermined amount of the allergen can be provided in the allergen source. For example, hair from a cat may be assayed to determine the concentration of the allergen in the hair, and then the hair may be provided in the allergen source in an amount that contains the desired amount of allergen. The predetermined amount of the allergen can be used to determine the symptoms of the subject in response to the predetermined amount, and various predetermined amounts can be used to determine a threshold amount of allergen that must be exceeded to induce the symptoms in the specific subject.

EXAMPLES

By way of example and not limitation, the following non-limiting examples are illustrative of apparatuses and methods of generating and measuring environmental levels of an allergen in embodiments provided by the present disclosure.

Example 1

A first experiment was performed regarding differential loading of environmental chambers using different mass amounts of cat hair from the same cat. Three environmental chambers were loaded with 1, 0.5 or 0.25 g of cat hair from the cat "Montana." Dust was collected using petri plates coated with 0.2% gelatin for 72 hours.

Figure 5:
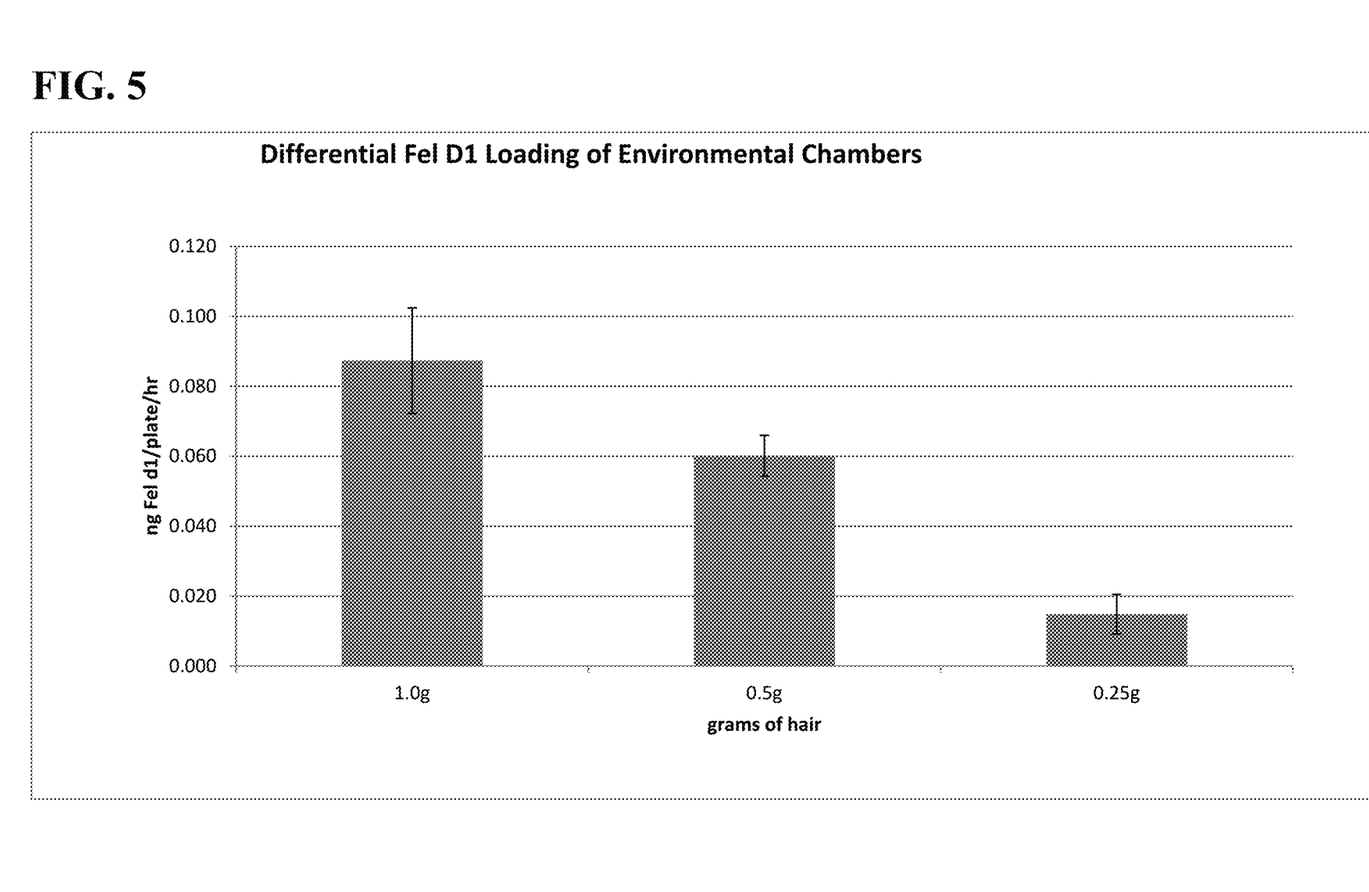
FIG. 5 is a graph of experimental results obtained in Example 1.

The dust was extracted from the petri plates and analyzed for Fel d1 using a commercially available ELISA kit (Indoor Pharmaceuticals). The level of Fel d1 was then normalized to time (ng Fel d1/plate/hour). Each dust collection was done in triplicate. Results are shown in the table below and FIG. 5 and show that the amount of allergen source corresponds closely to the level detected in the environmental chamber.

TABLE 1

| grams or hair | Fel d1 Levels in ECs ng Fel d1/plate/hr | SD |
|---|---|---|
| 1.0 g | 0.087 | 0.015 |
| 0.5 g | 0.060 | 0.006 |
| 0.25 g | 0.015 | 0.006 |

Example 2

A second experiment was performed in which three environmental chambers were loaded with 1 g of hair from three different cats, namely high, medium and low level Fel d1-producing cats. The level of Fel d1 for each cat was determined by measuring the Fel d1 in their hair and normalizing to mass amount of hair (ng Fel d1/mg hair). The hair from each cat was measured in triplicate.

Fel d1 levels in the cat hair used to load the environmental chambers are shown in the table below.

TABLE 2

| Cat | ng Fel d1/mg hair |
|---|---|
| Montana | 828 ng/mg hair |
| Stymie | 277 ng/mg hair |
| Koala | 16 ng/mg hair |

Figure 6:
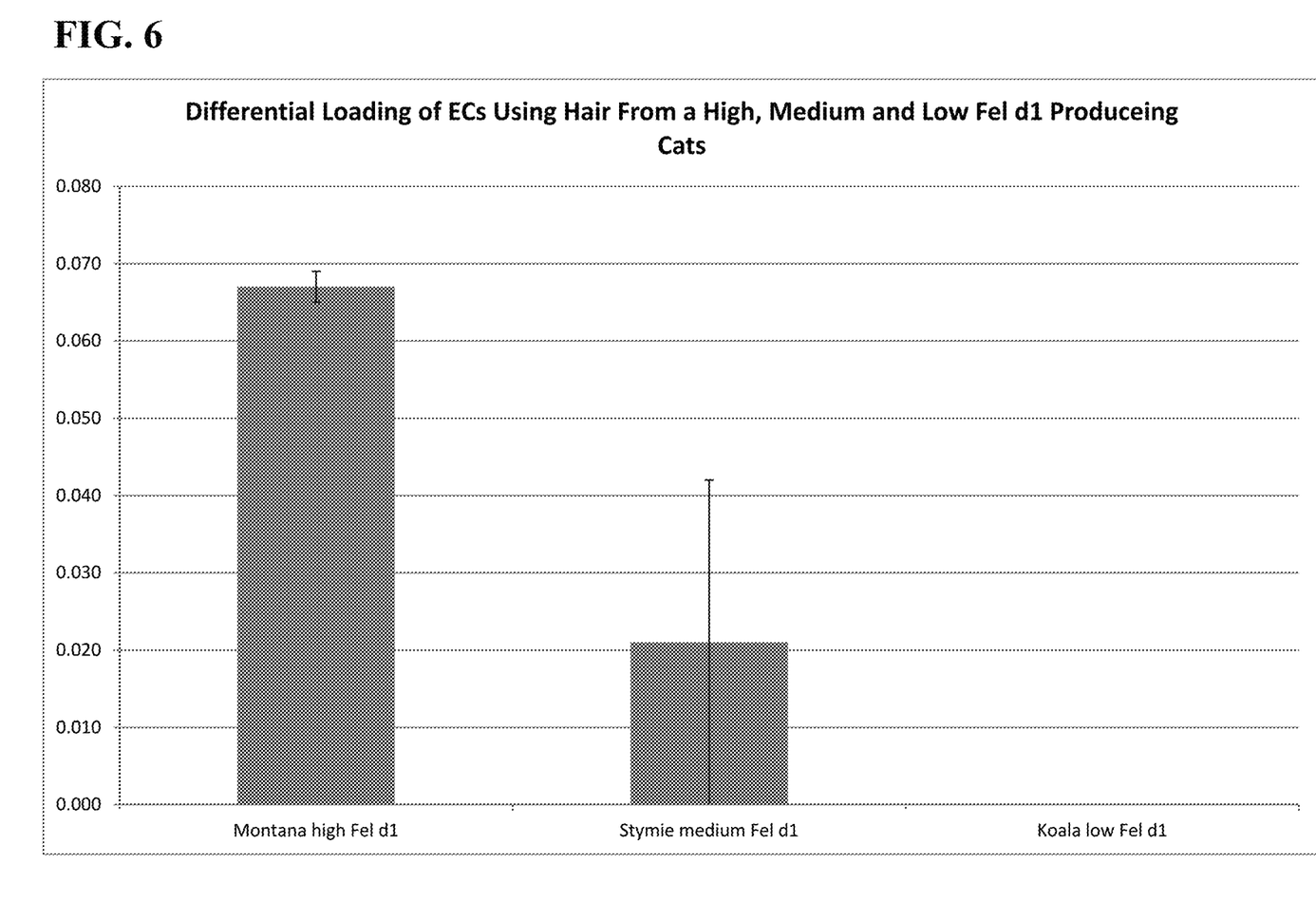
FIG. 6 is a graph of experimental results obtained in Example 2.

The dust was extracted from the petri plates and analyzed for Fel d1 as previously described in Example 1. Results are shown in the table below and FIG. 6 and show that the allergen production of the cat corresponds closely to the level detected in the environmental chamber.

TABLE 3

| Location | House Fel D1 levels ng Fel d1/plate/hr | SD |
|---|---|---|
| JL | 0.055 | 0.0076 |
| CT CR (cat) | 0.049 | 0.0028 |
| CT BR (no cat) | 0.009 | 0.0086 |

Example 3

Figure 7:
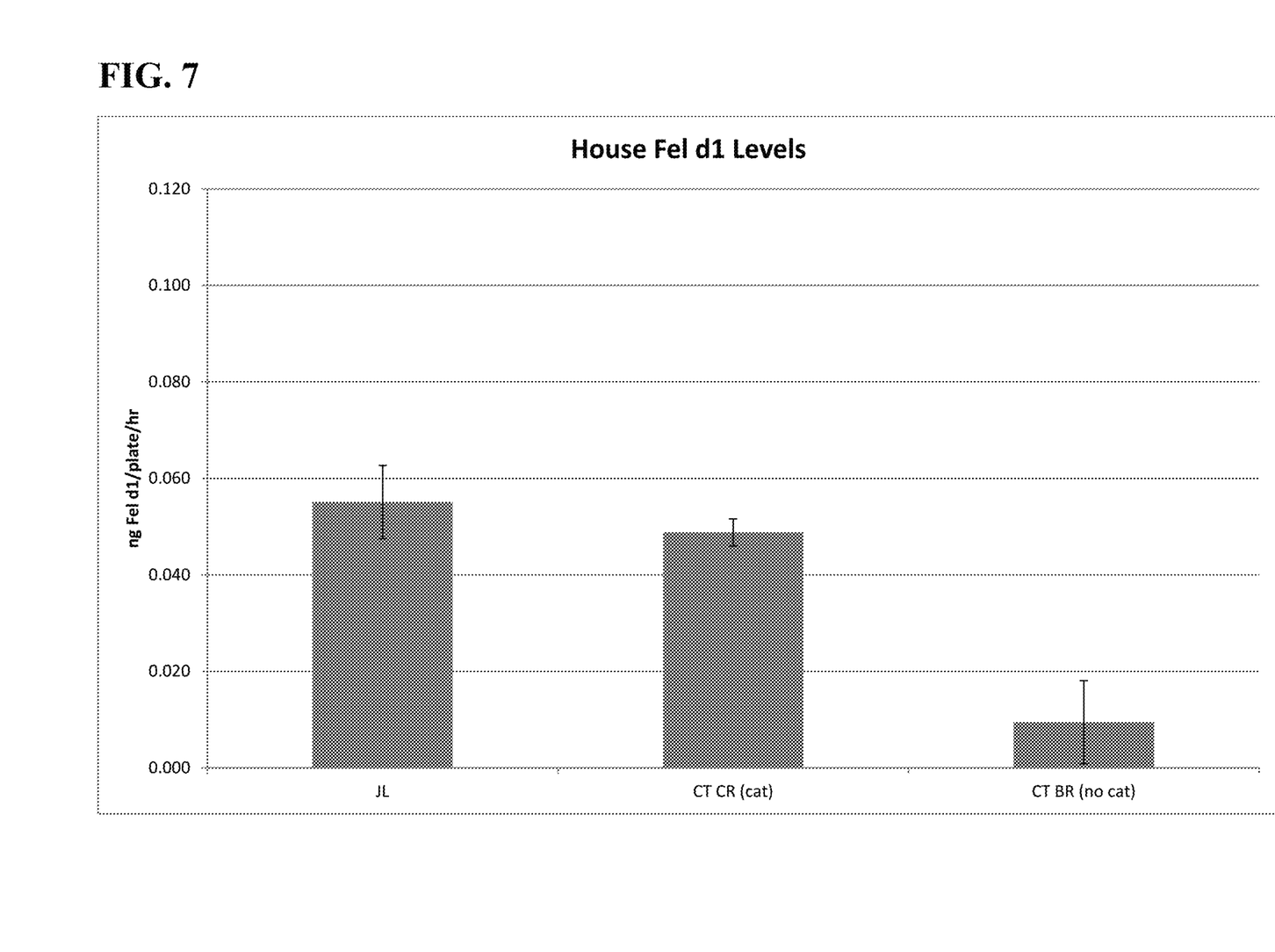
FIG. 7 is a graph of experimental results obtained in Example 3.

A third experiment was performed in which the level of Fel d1 in homes of cat owners was determined by collecting dust using the method described previously in Example 1. Dust was collected in "cat rooms" and "cat-free rooms" when possible in the same household. Dust was collected for 5 days (120 hours). Results are shown in the table below and FIG. 7 and show that the allergen production of the cat corresponds closely to the level detected in the environmental chamber.

TABLE 4

| Location | House Fel D1 levels ng Fel d1/plate/hr | SD |
|---|---|---|
| JL | 0.055 | 0.0076 |
| CT CR (cat) | 0.049 | 0.0028 |
| CT BR (no cat) | 0.009 | 0.0086 |

Example 4

Adult domestic shorthair cats were enrolled at two different locations: St. Joseph, Mo.—Study 1 (N=27) and Fergus, Ontario—Study 2 (N=37). Data collection started in the spring for Study 1 and in the fall for Study 2. In Study 1, 74% (N=20) of cats were male and 26% (N=7) were female. In Study 2, 19% (N=7) of cats were male and 81% (N=30) were female. All cats were either spayed or neutered. At the start of the study, the cats were on average 7.89 years old (SD=4.92) for Study 1 and 8.70 years old (SD=2.63) for Study 2. The cats weighed an average of 5.43 kg (SD=0.22) for Study 1 and 3.57 kg (SD=0.27) for Study 2. In addition to weight, the body condition score for each cat was measured. A body condition score was assigned to each cat based on a 9-point scale (1-3 too thin, 4-5 ideal, and 6-9 too heavy)

(Laflamme, 1997). The average BCS was 6.34 (SD=0.53) for Study 1 and 6.51 (SD=0.67) for Study 2.

In both studies, salivary Fel d1 was measured twice a day, every other day for a year duration. Not all the saliva collections were performed as planned, the cause of the interruptions included: unrelated health issues, moving cats into a new building, and the removal of cats due to their enrollment in concurrent studies.

The average number of days where salivary Fel d1 was measured was 144.43 (SD=11.25) for study 1 and 128.11 (SD=43.83) for study 2. Cats were measured at two points during the day, during the morning and during the afternoon.

Saliva collection was performed with commercially available Salivette® (Sarstedt, Nümbrecht, Germany) following the manufacturer's instructions (Park et al., 2008; Poll et al., 2007). Cat saliva samples were obtained by letting cats chew on Salivette that absorbs saliva. The saliva was then extracted by centrifuging the Salivettes, then they were stored at −80° C. until they were analyzed with a commercial Fel d1 ELISA kit (Indoor Technologies). The samples inventory of study 2 included if the amount of saliva collected was below 100 µl.

About 0.2 grams of hair was collected by grooming each cat with a new grooming brush. The hair was then stored in individual plastic bags at 2-8° C. until extraction. Extractions were performed in triplicates by weighing 15 to 30 mg of hair, then adding 200 µl of PBS 0.1% for each mg of hair. After overnight shaking, the supernatant was transferred to a new tube, centrifuged at 1000 g for 10 min, then transferred and centrifuged once again. The resulting supernatant was stored at −20° C. until it was analyzed with the same commercial Fel d1 ELISA kit used in measuring salivary Fel d1. The final result on the Fel d1 analysis was the average of the 3 extracts per hair collection.

To examine the relationship between alternative methods of measuring Fel d1, a comparison was done between salivary and hair Fel d1 measures using a subset of cats from study 1. These two were strongly related to each other (r=0.85, p<0.01), even though there was a year gap between when the salivary Fel d1 and hair Fel d1 were collected.

Saliva data (µg Fel d1/ml of saliva) collected twice daily every other day over a year from study 1 and study 2 is presented in table 5. Saliva data (µg Fel d1/ml of saliva) collected once daily every other day over a year from Study 1 and Study 2 is presented in table 6.

TABLE 5

|  | Study 1 | | | Study 2 | | |
| --- | --- | --- | --- | --- | --- | --- |
|  | Average (µg Fel d1/ml of saliva) | Number of measures | Number of cats | Average (µg Fel d1/ml of saliva) | Number of measures | Number of cats |
| January | 5.84 | 590 | 24 | 11.35 | 907 | 37 |
| February | 5.08 | 528 | 16 | 10.54 | 926 | 37 |
| March | 4.50 | 416 | 16 | 7.48 | 902 | 37 |
| April | 4.70 | 542 | 23 | 7.37 | 923 | 37 |
| May | 6.38 | 958 | 26 | 6.60 | 956 | 37 |
| June | 6.73 | 604 | 24 | 6.36 | 950 | 37 |
| July | 7.12 | 612 | 24 | 7.56 | 897 | 37 |
| August | 7.18 | 635 | 24 | 5.83 | 1013 | 37 |
| September | 7.50 | 565 | 24 | 6.53 | 857 | 37 |
| October | 6.97 | 606 | 24 | 5.82 | 977 | 37 |
| November | 7.19 | 240 | 24 | 8.65 | 953 | 37 |
| December | 5.85 | 624 | 24 | 15.37 | 720 | 37 |

TABLE 6

|  | Study 1 | | | Study 2 | | |
| --- | --- | --- | --- | --- | --- | --- |
|  | Average (µg Fel d1/ml of saliva) | Number of measures | Number of cats | Average (µg Fel d1/ml of saliva) | Number of measures | Number of cats |
| January | 6.50 | 295 | 24 | 12.68 | 461 | 37 |
| February | 5.51 | 264 | 16 | 12.13 | 465 | 37 |
| March | 4.76 | 208 | 16 | 8.30 | 443 | 37 |
| April | 5.04 | 271 | 23 | 8.11 | 465 | 37 |
| May | 6.63 | 479 | 26 | 7.12 | 479 | 37 |
| June | 7.25 | 302 | 24 | 7.35 | 477 | 37 |
| July | 8.02 | 306 | 24 | 8.16 | 454 | 37 |
| August | 7.89 | 318 | 24 | 6.08 | 506 | 37 |
| September | 8.32 | 283 | 24 | 6.82 | 432 | 37 |
| October | 7.69 | 303 | 24 | 6.63 | 496 | 37 |
| November | 7.70 | 120 | 24 | 9.05 | 486 | 37 |
| December | 6.24 | 312 | 24 | 17.55 | 354 | 37 |

As shown in Table 5 and 6, the expression of Fel d1 varied monthly. In one aspect, the higher expression time period can be from November to February. In another aspect, the high expression time period can be from July to September. Additionally, individual expressions for each cat is shown in Table 7 and 8, shown in µg/ml (microgram Fel d1 per ml of saliva). Saliva data (µg Fel d1/ml of saliva) collected twice daily every other day over a year from Study 1 and Study 2 is presented in table 7. Saliva data (µg Fel d1/ml of saliva) collected once daily every other day over a year from Study 1 and Study 2 is presented in table 8.

TABLE 7

| Cat ID | Average (µg/ml) |
| --- | --- |
| Cat #1 | 0.36 |
| Cat #2 | 0.49 |
| Cat #3 | 1.02 |
| Cat #4 | 1.08 |
| Cat #5 | 1.14 |
| Cat #6 | 1.20 |
| Cat #7 | 1.24 |
| Cat #8 | 1.52 |
| Cat #9 | 1.61 |
| Cat #10 | 1.74 |
| Cat #11 | 2.11 |
| Cat #12 | 2.11 |
| Cat #13 | 2.53 |
| Cat #14 | 2.54 |
| Cat #15 | 2.58 |
| Cat #16 | 3.01 |
| Cat #17 | 3.30 |
| Cat #18 | 3.44 |
| Cat #19 | 3.88 |
| Cat #20 | 3.95 |
| Cat #21 | 3.98 |
| Cat #22 | 3.99 |
| Cat #23 | 4.16 |
| Cat #24 | 4.17 |
| Cat #25 | 4.22 |
| Cat #26 | 4.24 |
| Cat #27 | 4.36 |
| Cat #28 | 4.46 |
| Cat #29 | 4.54 |
| Cat #30 | 4.64 |
| Cat #31 | 4.95 |
| Cat #32 | 5.04 |
| Cat #33 | 5.29 |
| Cat #34 | 5.72 |
| Cat #35 | 5.76 |
| Cat #36 | 6.42 |
| Cat #37 | 6.50 |
| Cat #38 | 6.62 |
| Cat #39 | 6.68 |

TABLE 7-continued

| Cat ID | Average (µg/ml) |
|---|---|
| Cat #40 | 6.80 |
| Cat #41 | 7.29 |
| Cat #42 | 7.87 |
| Cat #43 | 8.04 |
| Cat #44 | 8.20 |
| Cat #45 | 8.71 |
| Cat #46 | 8.50 |
| Cat #47 | 9.36 |
| Cat #48 | 9.27 |
| Cat #49 | 9.28 |
| Cat #50 | 9.38 |
| Cat #51 | 11.07 |
| Cat #52 | 11.44 |
| Cat #53 | 11.78 |
| Cat #54 | 11.87 |
| Cat #55 | 14.19 |
| Cat #56 | 15.02 |
| Cat #57 | 14.80 |
| Cat #58 | 16.61 |
| Cat #59 | 17.11 |
| Cat #60 | 18.34 |
| Cat #61 | 20.47 |
| Cat #62 | 21.99 |
| Cat #63 | 23.36 |
| Cat #64 | 35.04 |

TABLE 8

| Cat ID | Average (µg/ml) |
|---|---|
| Cat #1 | 0.37 |
| Cat #2 | 0.50 |
| Cat #3 | 1.10 |
| Cat #4 | 1.10 |
| Cat #5 | 1.28 |
| Cat #6 | 1.38 |
| Cat #7 | 1.38 |
| Cat #8 | 1.64 |
| Cat #9 | 1.72 |
| Cat #10 | 1.88 |
| Cat #11 | 2.03 |
| Cat #12 | 2.13 |
| Cat #13 | 2.70 |
| Cat #14 | 2.59 |
| Cat #15 | 2.55 |
| Cat #16 | 3.01 |
| Cat #17 | 3.35 |
| Cat #18 | 3.70 |
| Cat #19 | 4.20 |
| Cat #20 | 4.57 |
| Cat #21 | 4.03 |
| Cat #22 | 4.07 |
| Cat #23 | 4.54 |
| Cat #24 | 4.42 |
| Cat #25 | 4.32 |
| Cat #26 | 4.48 |
| Cat #27 | 4.63 |
| Cat #28 | 4.83 |
| Cat #29 | 5.05 |
| Cat #30 | 4.80 |
| Cat #31 | 5.42 |
| Cat #32 | 5.42 |
| Cat #33 | 5.60 |
| Cat #34 | 5.90 |
| Cat #35 | 5.50 |
| Cat #36 | 6.91 |
| Cat #37 | 6.57 |
| Cat #38 | 7.49 |
| Cat #39 | 7.61 |
| Cat #40 | 6.59 |
| Cat #41 | 7.85 |
| Cat #42 | 7.23 |
| Cat #43 | 8.33 |
| Cat #44 | 8.81 |
| Cat #45 | 8.84 |
| Cat #46 | 9.29 |
| Cat #47 | 11.41 |
| Cat #48 | 11.91 |
| Cat #49 | 10.92 |
| Cat #50 | 10.56 |
| Cat #51 | 12.59 |
| Cat #52 | 12.45 |
| Cat #53 | 12.11 |
| Cat #54 | 15.60 |
| Cat #55 | 15.26 |
| Cat #56 | 17.60 |
| Cat #57 | 15.77 |
| Cat #58 | 18.20 |
| Cat #59 | 17.67 |
| Cat #60 | 19.71 |
| Cat #61 | 23.22 |
| Cat #62 | 24.34 |
| Cat #63 | 25.20 |
| Cat #64 | 42.45 |

As shown in Tables 7 and 8, felines produce Fel d1 in varying amounts. As such, low, medium, and high Fel d1 producers can be quantified. Low Fel d1 producers can include felines that produce Fel d1 in an amount ranging from 0.01 to 5 micrograms per ml of saliva (µg/ml). Medium Fel d1 producers can include felines that produce Fel d1 in an amount ranging from between 5 and 10 micrograms per ml of saliva (µg/ml). High Fel d1 producers can include felines that produce Fel d1 in an amount from 10 to 100 micrograms per ml of saliva (µg/ml). Felines producing more than 100 micrograms per ml of saliva can also be deemed high Fel d1 producers.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of enabling an individual having a cat allergy to have a specific cat as a pet, the method comprising:
   using a primary fan and a secondary fan to suspend and/or distribute a FelD1 allergen aerosolized by the specific cat, wherein the primary fan directs air in a first direction at and/or across an allergen source comprising the FelD1 allergen, and the secondary fan directs air at and/or across the allergen source in at least a second direction opposite to the first direction, to produce air turbulence adjacent to and/or above the allergen source such that the air turbulence maintains particles from the allergen source in suspension;
   measuring an amount of the FelD1 allergen aerosolized by the specific cat; and
   selecting the specific cat as a pet for the individual if the amount of FelD1 aerosolized by the specific cat is less than an amount of FelD1 which induces allergic symptoms in the individual.

2. The method of claim 1, further comprising identifying one or more portions of the year having a higher expression of FelD1 allergen relative to at least one other portion of the year, and subsequently the measuring of the amount of the FelD1 allergen aerosolized by the specific cat is performed in at least one of the one or more portions of the year having a higher expression of FelD1 allergen.

3. The method of claim 1, further comprising quantitatively determining the amount of FelD1 which induces allergic symptoms in the individual by (i) measuring a quantity of the FelD1 in cat hair from a different cat, (ii) positioning the cat hair in a chamber, (iii) distributing the quantity of the FelD1 from the cat hair in the chamber, (iv) having the individual in the chamber, and (v) measuring the allergic symptoms of the individual.

4. The method of claim 3, wherein the individual is symptomatic from the quantity of the FelD1 distributed from the cat hair in the chamber, thereby identifying the amount of FelD1 which induces allergic symptoms in the individual.

5. The method of claim 1, wherein the suspending and/or distributing of the FelD1 allergen is performed for a predetermined time period.

6. The method of claim 1, wherein the allergen source is selected from the group consisting of an open container in which cat hair from the specific cat is positioned and a litter box containing litter soiled by the specific cat.

* * * * *